(12) United States Patent
Garred et al.

(10) Patent No.: US 9,012,154 B2
(45) Date of Patent: Apr. 21, 2015

(54) FICOLIN-3 ASSAY

(75) Inventors: Peter Garred, Charlottenlund (DK); Christian Honore, Cambridge, MA (US)

(73) Assignees: Rigshospitalet, Copenhagen Ø (DK); University of Copenhagen, Copenhagen K (DK)

( * ) Notice: Subject to any disclaimer, the term of this patent is extended or adjusted under 35 U.S.C. 154(b) by 447 days.

(21) Appl. No.: 13/377,121

(22) PCT Filed: Jun. 9, 2010

(86) PCT No.: PCT/DK2010/050129
§ 371 (c)(1),
(2), (4) Date: Dec. 28, 2011

(87) PCT Pub. No.: WO2010/142295
PCT Pub. Date: Dec. 16, 2010

(65) Prior Publication Data
US 2012/0101004 A1 Apr. 26, 2012

(30) Foreign Application Priority Data
Jun. 10, 2009 (DK) .................................. 2009 00725

(51) Int. Cl.
*G01N 33/53* (2006.01)
*G01N 33/564* (2006.01)

(52) U.S. Cl.
CPC ...... *G01N 33/564* (2013.01); *G01N 2333/4716* (2013.01)

(58) Field of Classification Search
None
See application file for complete search history.

(56) References Cited

FOREIGN PATENT DOCUMENTS

| WO | WO 2004011674 A1 * | 2/2004 |
|----|----|----|
| WO | 2005051662 A2 | 6/2005 |
| WO | 2006077248 A1 | 7/2006 |
| WO | WO 2009030240 A2 * | 3/2009 |
| WO | 2010142295 A1 | 12/2010 |

OTHER PUBLICATIONS

International Preliminary Report on Patentability; PCT/DK2010/050129 dated Dec. 12, 2011.
Tsujimura et al.; Detection of serum thermolabile beta-2 marcroglycoprotein (Hakata antigen) by enzyme-linked immunosorbent assay using polysaccharide produced by *Aerococcus viridans*; Clinical and Daiagnostic Laboratory Immunology; vol. 8, No. 2; 2001; pp. 454-459.
Hein, et al.; Development of a functional assay specific for Ficolin-3 mediated complement activation; Molecular Immunology; vol. 46, No. 14; Sep. 2009; p. 2843.
Garred, et al.; MBL2, FCN1, FCN2 and FCN3—The genes behind the initiation of the lectin pathway of complement; Molecular Immunology; vol. 46, No. 14; Jun. 2009; pp. 2737-2744.
Thiel et al.; Complement activating soluble pattern recognition molecules with collagen-like regions, mannan-binding lectin, ficolins and associated proteins; Molecular Immunology; vol. 44, No. 16; Sep. 1, 2007; pp. 3875-3888.
Thielens, et al.; Ficolins: Innate immune recognition proteins for danger sensing; Inmunologia; vol. 26, No. 3, Jul. 2007; pp. 145-156.
Written Opinion; PCT/DK2010/051029 dated Aug. 5, 2010.
International Search Report; PCT/DK2010/050129 dated Aug. 5, 2010.

* cited by examiner

*Primary Examiner* — Jim Ketter
(74) *Attorney, Agent, or Firm* — TraskBritt, P.C.

(57) ABSTRACT

The present invention relates to methods for detecting Ficolin-3 dependent activation of the lectin pathway of complement, methods for identifying abnormalities in Ficolin-3, and methods for screening for deficiencies/and or identifying abnormalities in any downstream components of the Ficolin-3 dependent activation of the lectin pathway of 5 complement using an acetylated Ficolin-3 ligand, said methods generally comprising the steps of: (a) providing a sample of blood, serum, plasma, another body fluid or an extract thereof; (b) (optionally) preventing in the sample activation of the classical pathway and/or the alternative pathway and/or any non-Ficolin-3 mediated activation of the lectin pathway; (c) acetylating a molecule; (d) contacting said acetylated molecule 10 with said sample, in conditions that permit specific binding of Ficolin-3 to said acetylated molecule, and, (e) detecting and quantifying specific binding of the Ficolin-3 to said acetylated molecule, (f) determining in the sample complement activation and/or deposition by the detection of a C2, C3, C4 and/or a C5 cleavage product and/or by detecting any of the terminal complement complex components C6, C7, C8 or C9 or 15 the C5b-9 terminal complement complex as such. The present invention also provides assays and kits comprising the methods of the invention.

14 Claims, 3 Drawing Sheets

SEQUENCE LISTING

```
<160> NUMBER OF SEQ ID NOS: 2

<210> SEQ ID NO 1
<211> LENGTH: 299
<212> TYPE: PRT
<213> ORGANISM: Homo sapiens

<400> SEQUENCE: 1

Met Asp Leu Leu Trp Ile Leu Pro Ser Leu Trp Leu Leu Leu Leu Gly
1               5                   10                  15

Gly Pro Ala Cys Leu Lys Thr Gln Glu His Pro Ser Cys Pro Gly Pro
            20                  25                  30

Arg Glu Leu Glu Ala Ser Lys Val Val Leu Leu Pro Ser Cys Pro Gly
        35                  40                  45

Ala Pro Gly Ser Pro Gly Glu Lys Gly Ala Pro Gly Pro Gln Gly Pro
    50                  55                  60

Pro Gly Pro Pro Gly Lys Met Gly Pro Lys Gly Glu Pro Gly Asp Pro
65                  70                  75                  80

Val Asn Leu Leu Arg Cys Gln Glu Gly Pro Arg Asn Cys Arg Glu Leu
                85                  90                  95

Leu Ser Gln Gly Ala Thr Leu Ser Gly Trp Tyr His Leu Cys Leu Pro
            100                 105                 110
```

```
Glu Gly Arg Ala Leu Pro Val Phe Cys Asp Met Asp Thr Glu Gly Gly
            115                 120                 125

Gly Trp Leu Val Phe Gln Arg Gln Asp Gly Ser Val Asp Phe Phe Arg
    130                 135                 140

Arg Ser Trp Ser Ser Tyr Arg Ala Gly Phe Gly Asn Gln Glu Ser Glu
145                 150                 155                 160

Phe Trp Leu Gly Asn Glu Asn Leu His Gln Leu Thr Leu Gln Gly Asn
                165                 170                 175

Trp Glu Leu Arg Val Glu Leu Glu Asp Phe Asn Gly Asn Arg Thr Phe
            180                 185                 190

Ala His Tyr Ala Thr Phe Arg Leu Leu Gly Glu Val Asp His Tyr Gln
            195                 200                 205

Leu Ala Leu Gly Lys Phe Ser Glu Gly Thr Ala Gly Asp Ser Leu Ser
            210                 215                 220

Leu His Ser Gly Arg Pro Phe Thr Thr Tyr Asp Ala Asp His Asp Ser
225                 230                 235                 240

Ser Asn Ser Asn Cys Ala Val Ile Val His Gly Ala Trp Trp Tyr Ala
                245                 250                 255

Ser Cys Tyr Arg Ser Asn Leu Asn Gly Arg Tyr Ala Val Ser Glu Ala
            260                 265                 270

Ala Ala His Lys Tyr Gly Ile Asp Trp Ala Ser Gly Arg Gly Val Gly
            275                 280                 285

His Pro Tyr Arg Arg Val Arg Met Met Leu Arg
            290                 295

<210> SEQ ID NO 2
<211> LENGTH: 288
<212> TYPE: PRT
<213> ORGANISM: Homo sapiens

<400> SEQUENCE: 2

Met Asp Leu Leu Trp Ile Leu Pro Ser Leu Trp Leu Leu Leu Leu Gly
1                   5                   10                  15

Gly Pro Ala Cys Leu Lys Thr Gln Glu His Pro Ser Cys Pro Gly Pro
                20                  25                  30

Arg Glu Leu Glu Ala Ser Lys Val Val Leu Leu Pro Ser Cys Pro Gly
            35                  40                  45

Ala Pro Gly Ser Pro Gly Glu Lys Gly Ala Pro Gly Pro Gln Gly Pro
        50                  55                  60

Pro Gly Pro Pro Gly Lys Met Gly Pro Lys Gly Glu Pro Gly Pro Arg
65                  70                  75                  80

Asn Cys Arg Glu Leu Leu Ser Gln Gly Ala Thr Leu Ser Gly Trp Tyr
                85                  90                  95

His Leu Cys Leu Pro Glu Gly Arg Ala Leu Pro Val Phe Cys Asp Met
                100                 105                 110

Asp Thr Glu Gly Gly Gly Trp Leu Val Phe Gln Arg Arg Gln Asp Gly
            115                 120                 125

Ser Val Asp Phe Phe Arg Ser Trp Ser Ser Tyr Arg Ala Gly Phe Gly
        130                 135                 140

Asn Gln Glu Ser Glu Phe Trp Leu Gly Asn Glu Asn Leu His Gln Leu
145                 150                 155                 160

Thr Leu Gln Gly Asn Trp Glu Leu Arg Val Glu Leu Glu Asp Phe Asn
                165                 170                 175

Gly Asn Arg Thr Phe Ala His Tyr Ala Thr Phe Arg Leu Leu Gly Glu
```

-continued

```
                    180                 185                 190
Val Asp His Tyr Gln Leu Ala Leu Gly Lys Phe Ser Glu Gly Thr Ala
        195                 200                 205

Gly Asp Ser Leu Ser Leu His Ser Gly Arg Pro Phe Thr Thr Tyr Asp
        210                 215                 220

Ala Asp His Asp Ser Ser Asn Ser Asn Cys Ala Val Ile Val His Gly
225                 230                 235                 240

Ala Trp Trp Tyr Ala Ser Cys Tyr Arg Ser Asn Leu Asn Gly Arg Tyr
                245                 250                 255

Ala Val Ser Glu Ala Ala His Lys Tyr Gly Ile Asp Trp Ala Ser
                260                 265                 270

Gly Arg Gly Val Gly His Pro Tyr Arg Arg Val Arg Met Met Leu Arg
                275                 280                 285
```

FICOLIN-3 ASSAY

CROSS-REFERENCE TO RELATED APPLICATIONS

This is a national phase entry under 35 U.S.C §371 of International Patent Application PCT/DK2010/050129, filed Jun. 9, 2010, published in English as International Patent Publication WO 2010/142295 A1 on Dec. 16, 2010, which claims the benefit under Article 8 of the Patent Cooperation Treaty to Denmark Patent Application Serial No. PA 2009 00725, filed Jun. 10, 2009.

All patent and non-patent references cited in the application, or in the present application, are also hereby incorporated by reference in their entirety.

FIELD OF INVENTION

The present invention relates to methods for detecting Ficolin-3 dependent activation of the lectin pathway of complement, methods for identifying abnormalities in Ficolin-3, and methods for screening for deficiencies/and or identifying abnormalities in any downstream components of the Ficolin-3 dependent activation of the lectin pathway of complement using an acetylated Ficolin-3 ligand, said methods generally comprising the steps of: (a) providing a sample of blood, serum, plasma, another body fluid or an extract thereof; (b) (optionally) preventing in the sample activation of the classical pathway and/or the alternative pathway and/or any non-Ficolin-3 mediated activation of the lectin pathway; (c) acetylating a molecule; (d) contacting said acetylated molecule with said sample, in conditions that permit specific binding of Ficolin-3 to said acetylated molecule, and, (e) detecting and quantifying specific binding of the Ficolin-3 to said acetylated molecule, (f) determining in the sample complement activation and/or deposition by the detection of a C2, C3, C4 and/or a C5 cleavage product and/or by detecting any of the terminal complement complex components C6, C7, C8 or C9 or the C5b-9 terminal complement complex as such.

The present invention also provides assays and kits comprising the methods of the invention.

BACKGROUND OF INVENTION

The complement system is part of the innate immune system, which protects the body against invading pathogens. Initiator molecules of complement system recognize conserved patterns on the surface of microorganisms, which then initiates a cascade of enzymatic reactions. This results in targeted removal and in some cases destruction of the microorganisms. Three activation pathways of the complement system have been described; the classical pathway, the alternative pathway and the lectin pathway. C1q activates the classical pathway; the alternative pathway is activated by spontaneous hydrolysis of C3 and in some cases properdin. The lectin pathway is activated by mannose-binding lectin (MBL) and the Ficolins (Ficolin-1, Ficolin-2 and Ficolin-3). Ficolin-1 is expressed by cells of myeloid origin and is found circulating in serum at low concentrations. Ficolin-2 and Ficolin-3 are both expressed in the liver and are circulating in serum at a mean concentration of 5 µg/ml and 24 µg/ml, respectively. Furthermore, Ficolin-3 is abundantly expressed in the lungs, suggesting a role for this molecule in pulmonary immune defence.

In humans, three ficolin genes have been identified: FCN1, FCN2 and FCN3, which encode Ficolin-1 (synonymous with M-ficolin and Ficolin/P35-related protein), Ficolin-2 (synonymous with L-ficolin, Ficolin/P35 and Hucolin) and Ficolin-3 (synonymous with H-ficolin, Hakata antigen and thermolabile β2-macroglycoprotein, HAKA1, collagen/fibinogen domain-containing lectin 3 P35), respectively. FCN1 and FCN2 are both located on chromosome 9q34, and are 80% homologous at the amino acid level, whereas FCN3 is assigned to chromosome 1 (1p36.11, 1p35.3) ((Endo, Y., et al. (1996), Sugimoto, R. et al., (1998)).

On the amino acid level, Ficolin-3 reveals ~40% homology with both Ficolin-1 and Ficolin-2. FCN1 contains nine exons, whereas FCN2 and FCN3 are composed of eight exons. Ficolin-2 and Ficolin-3 are found in serum and exhibits inter-individual variation in serum concentrations (Kilpatrick, D. C. et al., (1999), Matsushita, M. et al., (1996), Yae Y., et al., (1991)). FCN2 is predominantly expressed in the liver and FCN3 in the liver and lung (Endo, Y., et al. (1996), Akaiwa, M., et al., (1999)). Ficolin-1 is expressed in the lung, the spleen and by undifferentiated monocytes (Endo, Y., et al. (1996), Harumiya, S., et al., (1996), Lu, J., et al., (1996)). Ficolin-1 is present in serum in lower concentrations (Honore, C., et al (2008)).

The ficolins are synthesized as a single polypeptide containing N-terminal collagen-like and C-terminal fibrinogen-like sugar-binding domains, which are oligomerized into higher oligomeric forms comprising triple helix structures (Matsushita, M., Fujita, T. (2001)). The collagen-like multimeric structure is shared with C1q, mannose-binding lectin (MBL) and surfactants proteins A and D (SP-A and SP-D).

The fibrinogen-like domains of Ficolin-1 and Ficolin-2 have been shown to interact with carbohydrates, such as N-acetylglucosamine (GlcNAc) (Teh, C., et al., (2000)).

Moreover, a general specificity for N-acetylated groups for Ficolin-2 has also been demonstrated (Krarup, A., et al., (2004)). Both Ficolin-1 and Ficolin-2 appear to bind to different types of bacteria and Ficolin-2 may specifically bind to lipoteichoic acid from gram-positive bacteria (Teh, C., et al., (2000), Lynch, N. J., et al., (2004)). The ligands for Ficolin-3 are unknown, but distinct binding to certain strains of bacteria has been demonstrated (Tsujimura, M., et al., (2002)). Ficolin-1 has been shown to enhance uptake of bacteria to monocytes and Ficolin-2 and Ficolin-3 have been shown to interact with the Ficolin-3-associated serine proteases enabling activation of the complement system (Teh, C., et al., (2000), Matsushita, M., et al., (2000), Matsushita, M., et al., (2002)). Taken together, these results provide evidence for the fact that the ficolins are important molecules in imparting innate immunity.

Conventional functional assays for evaluating complement activation through the different pathways mostly use an MBL-specific ligand for assessing the lectin pathway. WO/2005/051662 describes methods for detecting Ficolin-2 dependent activation of the lectin pathway.

Recently a frameshift mutation (FCN3+1637delC) in the gene (FCN3) encoding Ficolin-3 was described (Hummelshoj, T., et al (2005)). This mutation results in premature termination leading to expression of a non-functional protein. Individuals heterozygous for the FCN3+1637delC mutation showed significantly lower levels of Ficolin-3 in serum and from studies using recombinant protein expression it was found that an individual homozygous for this mutation would result in Ficolin-3 deficiency (Munthe-Fog, L., et al (2008)).

The allele frequency of this mutation was 0.011 in Caucasians, meaning that homozygosity for the FCN3+1637delC mutation will be found in approximately 1 out of 8000-10,000 individuals. The frameshift mutation (FCN3+1637delC) was analysed in are large group of patients with suspected non-HIV related primary immunodeficiencies. We identified one patient that was homozygous for the FCN3+1637delC allele. This patient suffered from unexplained recurrent bacterial lung infections, brochiectasis, lung fibrosis and obstructive lung disease and had experienced one incidence of cerebral abscesses. Thus, Ficolin-3 deficiency appears to result in a novel complement deficiency state. This observation calls for an assay that can identify functional and genetic deficiencies of Ficolin-3.

SUMMARY OF INVENTION

The applicants herein describe novel methods using the novel finding that Ficolin-3 binds to acetylated molecules and at the same time mediate activation of C4, which is not the case for ficolin-1 and ficolin-2 to any substantial degree. While binding to acetylated compounds are well known for ficolin-1 and ficolin-2, it was a surprise that ficolin-3 was a very efficient ligand for ficolin-3 in order to mediate complement deposition since very few ficolin-3 ligands have been described. Based on this finding an assay was developed that screens specifically for Ficolin-3 mediated complement activation. Not only will this assay identify individuals carrying genetic or functional deficiencies in Ficolin-3, but it will also be applicable for screening for deficiencies in the MBL-associated serine proteases (MASPs) and other downstream components of the complement system.

The invention demonstrates that an acetylated molecule immobilized on a support can be used as a specific assay for screening for functional or genetic deficiencies in Ficolin-3. Furthermore, the assay will also identify individuals deficient in the serine proteases (MASPs) involved in Ficolin-3 mediated complement activation. Measuring complement activation products downstream of Ficolin-3/MASP such as C4 will also enable this assay to screen for deficiencies in other complement components A first aspect of the present invention relates to method for detecting Ficolin-3 dependent activation of the lectin pathway of complement comprising and/or for identifying an abnormality in Ficolin-3 and/or for identifying an abnormality in any downstream components of the Ficolin-3 dependent activation of complement using an acetylated Ficolin-3 ligand.

Another aspect of the invention relates to a method for detecting Ficolin-3 dependent activation of the lectin pathway of complement and/or for identifying an abnormality in Ficolin-3 and/or for identifying an abnormality in any downstream components of the Ficolin-3 dependent activation of complement comprising the steps of:
a. providing a sample of blood, serum, plasma, another body fluid or an extract thereof;
b. (optionally) preventing in the sample activation of the classical pathway and/or the alternative pathway and/or any non-Ficolin-3 mediated activation of the lectin pathway;
c. providing an acetylated molecule;
d. contacting said acetylated molecule with said sample, in conditions that permit specific binding of Ficolin-3 to said acetylated molecule, and,
e. detecting and quantifying specific binding of the Ficolin-3 to said acetylated molecule;
f. determining in the sample complement activation and/or deposition by the detection of a C2, C3, C4 and/or a C5 cleavage product and/or by detecting any of the terminal complement complex components C5b, C6, C7, C8 or C9 or the C5b-9 complex.

A specific aspect of the invention relates to assays for detecting Ficolin-3 dependent activation of the lectin pathway of complement, comprising the methods described herein.

Another aspect of the invention relates to assays for identifying an abnormality in Ficolin-3.

Yet another aspect of the invention relates to assays for identifying an abnormality in any downstream components of the Ficolin-3 dependent activation of complement.

A specific aspect of the invention relates to a method for identifying a Ficolin-3 abnormality comprising any method or assay as described herein.

Another aspect of the invention relates to a method for identifying an abnormality in Ficolin-3 comprising any method or assay as described herein.

Yet another aspect of the invention relates to a method for identifying an abnormality in any downstream components of the Ficolin-3 dependent activation of complement. Other specific aspects of the invention relate to kits for performing any of the methods or assays described herein.

A specific embodiment of this aspect relates to a kit for detecting Ficolin-3 dependent activation of the lectin pathway of complement and/or for identifying an abnormality in Ficolin-3 and/or for identifying an abnormality in any downstream components of the Ficolin-3 dependent activation of complement comprising:
a. an acetylated molecule immobilised on a support,
b. full serum as a positive control
c. a reagent or reagents for detection of a complement cleavage product and/or by detecting any terminal complement complex, and
d. one or more buffers which allow binding of Ficolin-3 to an acetylated molecule
e. optionally standard serum or purified Ficolin-3/MASP complex suitable for generation of a standard curve, and,
f. optionally instructions for use of the kit.

In another embodiment of this aspect, the kit may comprise
a. an acetylated molecule immobilised on a support,
b. a purified C4 or crude C4/C3 preparation, and
c. a reagent or reagents for detection of a C3 and/or C4 cleavage product, and
d. one or more buffers which allows binding of ficolin-3 to an acetylated molecule
e. optionally standard serum or purified Ficolin-3/MASP complex suitable for generation of a standard curve, and,
f. optionally instructions for use of the kit.

Another specific embodiment of this aspect relates to a kit for detecting Ficolin-3 comprising:
a. an acetylated molecule immobilised on a support, and
b. a reagent or reagents for detection of Ficolin-3 binding to said acetylated molecule, and
c. one or more buffers which allows binding of ficolin-3 to an acetylated molecule
d. optionally, standard serum or purified Ficolin-3/MASP complex or purified Ficolin-3, suitable for generation of a standard curve, and
e. optionally, instructions for use of the kit

DEFINITIONS

Acetylated molecule: as used herein, is intended to mean any molecule that is acetylated, such as for example a protein or a carbohydrate.

Acetylation: as used herein, is intended to mean the addition of an acetyl functional group to an organic compound.

Alternative Pathway: as used herein, is intended to mean activation of complement via the spontaneous hydrolysis of the complement enzyme C3.

Biological sample: as used herein, is intended to mean a sample obtained from a subject or individual, such as blood, serum, plasma, another body fluid or an extract thereof.

Classical Pathway: as used herein, is intended to mean activation of complement via the binding of antigen-bound antibody molecules to the complement enzyme C1.

Cleavage assay: as used herein, is intended to mean any assay that determines the cleavage of a complement component such as C2, C3, C4 and/or a C5, thereby determining activation of complement. A cleavage assay may be specific for a particular complement component.

Cleavage product: C2, C3, C4 and/or a C5 are cleaved upon complement activation. A complement cleavage product as used herein is intended to mean any complement cleavage product including but not limited to C2, C3, C4 and/or a C5 cleavage products.

Conditions that permit specific binding of Ficolin-3 to an acetylated molecule: as used herein, is intended to mean any conditions under which Ficolin-3 will bind to an acetylated molecule including those described in the Examples such as hepes-buffer (25 mM Hepes, 155 mM NaCl, 5 mM $CaCl_2$, pH=7.4) containing 0.05% tween (hepes-T). Other buffers that permit conditions under which Ficolin-3 will bind to an acetylated molecule include but are not limited to Tris acetate buffer, tris buffer, phosphate buffered saline (PBS) buffers, veronal buffer saline, and barbital buffer such as for example another preferred buffer comprising Barbital-natrium 4.12 g/l, Natriumchlorid 42.50 g/l, Calciumchlorid 1.47 g/l, Magnesiumchlorid 1.01 g/lpH 7.4 and diluted 1:4 in $H_2O$ with a final dilution in 0.05% Tween 20.

Complement: as used herein, is intended to mean a biochemical cascade that helps clear pathogens from an organism. It is part of the larger immune system that is not adaptable and does not change over the course of an individual's lifetime; as such it belongs to the innate immune system.

Deposition of activated complement components: as used herein, is intended to mean a means for measuring activation of complement. In the assay described herein, complement components are only deposited if activated.

Detectable marker: as used herein, is intended to mean any marker used to label a ligand that may be detected.

Extract of blood, serum, plasma, another body fluid: as used herein, is intended to mean any extract or concentrate of said biological samples. Methods for making such extract or concentrate are well known in the art.

Ficolin: as used herein, is intended to mean a group of proteins, which consist of a collagen-like domain and a fibrinogen-like domain. Ficolins can activate the complement pathway in association with MASPs Ficolin-3 ligand: as used herein, is intended to mean any acetylated molecule that will bind Ficolin-3.

Individual: Any species or subspecies of bird, mammal, fish, amphibian, or reptile. Preferably a human being or a domesticated animal.

MBL: as used herein, is intended to mean Mannan-binding lectin or Mannose-binding lectin. MBL is a C-type lectin that can activate the lectin pathway of the complement system in innate immunity.

Lectin Pathway: as used herein, is intended to mean activation of complement via MBL or the ficolins.

One or more buffers, which allow binding of ficolin-3 to an acetylated molecule: as used herein, is intended to mean a buffer or a combination of one or more buffers providing conditions under which Ficolin-3 will bind to an acetylated molecule including those described in the Examples such as hepes-buffer (25 mM Hepes, 155 mM NaCl, 5 mM $CaCl_2$, pH=7.4) containing 0.05% tween (hepes-T). Other buffers that permit conditions under which Ficolin-3 will bind to an acetylated molecule include but are not limited to Tris acetate buffer, tris buffer, phosphate buffered saline (PBS) buffers, veronal buffer saline, and barbital buffer such as for example another preferred buffer comprising Barbital-natrium 4.12 g/l, Natriumchlorid 42.50 g/l, Calciumchlorid 1.47 g/l, Magnesiumchlorid 1.01 g/lpH 7.4 and diluted 1:4 in $H_2O$ with a final dilution in 0.05% Tween 20.

Support: A material having a rigid or semi-rigid surface. Such materials will preferably take the form of plates or slides, small beads, pellets, disks, capillary tubes or other convenient forms, although other forms may be used. In some embodiments, at least one surface of the solid support will be substantially flat. The solid support may be biological, non-biological, organic, inorganic, or a combination of any of these, existing as particles, strands, precipitates, gels, sheets, tubing, spheres, containers, capillaries, pads, slices, films, plates, slides, etc.

Terminal complement complex: as used herein, is intended to mean a complex of complement components C5b, C6, C7, C8 and C9 or any of the components not in a complex, but which also may contain clusterin and/or vitronectin. The terminal complement complex is also called the membrane attack complex (MAC).

DETAILED DESCRIPTION OF THE INVENTION

This method is based on the novel specific interaction Ficolin-3 and acetylated molecules.

The present invention describes a method for detecting Ficolin-3 dependent activation of the lectin pathway of complement comprising and/or for identifying an abnormality in Ficolin-3 and/or for identifying an abnormality in any downstream components of the Ficolin-3 dependent activation of complement using an acetylated Ficolin-3 ligand.

Specifically the present invention describes a method for detecting Ficolin-3 dependent activation of the lectin pathway of complement and/or for identifying an abnormality in Ficolin-3 and/or for identifying an abnormality in any downstream components of the Ficolin-3 dependent activation of complement comprising the steps of:

a. providing a sample of blood, serum, plasma, another body fluid or an extract thereof;
b. (optionally) preventing in the sample activation of the classical pathway and/or the alternative pathway and/or any non-Ficolin-3 mediated activation of the lectin pathway;
c. providing an acetylated molecule;
d. contacting said acetylated molecule with said sample, in conditions that permit specific binding of Ficolin-3 to said acetylated molecule, and,
e. detecting and quantifying specific binding of the Ficolin-3 to said acetylated molecule;

f. determining in the sample complement activation and/or deposition by the detection of a C2, C3, C4 and/or a C5 cleavage product and/or by detecting any of the terminal complement components C5b, C6, C7, C8 or C9 or the C5b-9 complex.

In one embodiment the method further comprises additional washing steps.

Thus a particular embodiment of the invention relates to a method for detecting Ficolin-3 dependent activation of the lectin pathway of complement, comprising any of the methods described herein.

Another particular embodiment of the invention relates to a method for identifying an abnormality in Ficolin-3, comprising any of the methods described herein.

Another particular embodiment of the invention relates to a method for identifying an abnormality in any downstream components of the Ficolin-3 dependent activation of complement, comprising any of the methods described herein.

Thus a particular embodiment of the invention relates to an assay for Ficolin-3 dependent activation of the lectin pathway of complement, comprising any of the methods described herein.

Another particular embodiment of the invention relates to an assay for identifying an abnormality in Ficolin-3, comprising any of the methods described herein.

Another particular embodiment of the invention relates to an assay for identifying an abnormality in any downstream components of the Ficolin-3 dependent activation of complement comprising any of the methods described herein.

The methods and assays described herein may be used to detect an abnormality in any downstream components of the Ficolin-3 dependent activation of complement. The downstream components of Ficolin-3 dependent activation of complement include but are not limited to any of the molecules selected from the group consisting of MASP-1, MASP-2, MASP-3, C2, C3, C4, C5, C6, C7, C8, C9, complement regulatory protein factor I, Factor H, C1 inhibitor and C4 binding protein.

Ficolin

The ficolins are a group of soluble animal proteins with roles in innate immunity. The classification of ficolins as lectins is controversial because the ligand binding domain in ficolins is specific for acetyl groups in both carbohydrates (eg GlcNAc, ManNAc, GalNAc) and non-carbohydrates (eg N-acetylglycine, N-acetylcysteine, acetylcholine).

Binding of sugars is not primarily dependent on the sugar ring, and sugars which do not contain acetyl groups are generally not ficolin ligands. However, many of the bacterial surface molecules which appear to be natural ligands for the ficolins contain carbohydrate moieties, and ficolins have similar functional properties to lectins.

A ficolin polypeptide consists of a small N-terminal domain, a collagen-like domain, a neck region, and a fibrinogen-like domain, which shows similarity to the C-terminal halves of the beta and gamma chains of fibrinogen. The collagen-like domain mediates the association of ficolin polypeptides into trimers, and the N-terminal domain contains cysteine residues, which permit the covalent assembly of Ficolin trimers into higher oligomers with a 'bouquet-like' appearance. This supramolecular organization resembles that of the collectins, a group of C-type lectins which have a C-type CRD in place of the fibrinogen-like domain found in ficolins. Collectins and ficolins are also functionally similar. The collectin mannose-binding lectin (MBL) is a serum host defence protein in which the C-type CRDs recognize arrays of GlcNAc and mannose residues on pathogen surfaces. MBL initiates the lectin branch of the complement system via activation of MBL-associated proteases (MASPs), leading to elimination of the target pathogen. Ficolin-1, ficolins-2 and ficolin-3, are also serum proteins which bind to pathogen surfaces via interaction with carbohydrates (and probably with other molecules), and trigger complement activation though association with MASPs. Ficolin-2 also acts as an opsonin, promoting phagocytosis of pathogens by neutrophils. Ficolin-2 polymorphisms affect serum protein levels and sugar binding and may have pathophysiological implications. The third human ficolin, ficolin-1, is found in secretory granules in neutrophils and monocytes, recognizes pathogens in a carbohydrate-dependent manner and activates complement via MASPs. Ficolin-1 may also act as a phagocytic receptor. Ficolins-2 and 3 are produced in the liver, in common with MBL, and ficolin-1 is produce bone marrow derived cells and in the lungs and ficolin-3 is also produced in the lung, like the antimicrobial collectins SP-A and SP-D. Human ficolins and MBL also participate in the recognition and clearance of apoptotic cells.

The ficolin according to the present invention may be any ficolin. In a preferred embodiment of the present invention, the ficolin is Ficolin-3.

Ficolin-3

The present invention concerns, in one embodiment, the detection of activation of the lectin pathway via Ficolin-3. Ficolin-3 may be of human origin, or may originate from other animal species in which the immune system in this respect is acting like the human immune system. In a preferred embodiment of the invention Ficolin-3 is of human origin.

The wild-type human Ficolin-3, i.e. the naturally occurring non-mutated version of the protein, is identified as SEQ ID NO:1. The present invention also covers variants and functional homologues of Ficolin-3 comprising a sequence identity of at least 80% to SEQ ID NO:1 (see details herein below).

A variant can be defined as a naturally occurring Ficolin-3 that differs in sequence from the wild-type Ficolin-3 of the same species, but is still functionally competent. A variant may be a mutated version or an alternative splice variant of the wild-type Ficolin-3 of the same species. In another aspect Ficolin-3 variants are defined as functional homologues as described herein below. A functional homologue may be, but is not limited to, a recombinant version of Ficolin-3 with one or more mutations and/or one or more sequence deletions and additions introduced ex vivo.

Ficolin-3 and Ficolin-3 Variants and Functional Homologues

The term Ficolin-3 in the present application designates wild type Ficolin-3 and Ficolin-3 variants. The term, wild-type Ficolin-3, designates the naturally occurring non-mutated version of the protein in a given species. Human wild-type Ficolin-3 is identified as SEQ ID NO. 1. In one preferred embodiment of the invention Ficolin-3 is human Ficolin-3, in a more preferred embodiment Ficolin-3 is human wild-type Ficolin-3 as identified by SEQ ID NO. 1. In a very preferred embodiment Ficolin-3 is recombinant wild type human Ficolin-3. Ficolin-3 variants include any form of Ficolin-3 known to a person skilled in the art and any functional homologue thereof. For example, Ficolin-3 variants include splice variants and allelic variants and single nucleotide polymorphisms. In particular, Ficolin-3 variants may be proteins comprising at least one polypeptide comprising the amino acid sequence identified as SEQ ID NO. 1 or a functional homologue thereof, specifically the variant may be an alternative splice variant as defined is SEQ ID NO: 2, wherein residues 79-89 are missing. A functional homologue of Ficolin-3 may be any protein that exhibits at least some sequence identity with SEQ ID NO. 1, and shares one or more functions with Ficolin-3, such as     capacity for activation of the lectin pathway of complement     capacity for binding to GlcNAc Ficolin-3 according to the present invention may comprise one or more subunits. A Ficolin-3 subunit normally consists of 2 or 3 individual polypeptides; preferably each individual polypeptide comprises an amino acid sequence as identified by SEQ ID NO. 1 or SEQ ID NO: 2 or a functional homologue thereof. For example Ficolin-3 may be monomers, dimers, trimers, tetramers, pentamers, hexamers, heptamers, octamers, nonamers, decamers, 11-mers, 12-mers of subunits or Ficolin-3 may comprise even more than 12 subunits.

Each polypeptide chain of a Ficolin-3 subunit comprises a C-terminal Fibrinogen C-like domain attached to a collagen-like domain.

Furthermore, a person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterised by having     i) polar side chains (Asp, Glu, Lys, Arg, His, Asn, Gln, Ser, Thr, Tyr, and Cys,)
    ii) non-polar side chains (Gly, Ala, Val, Leu, Ile, Phe, Trp, Pro, and Met)
    iii) aliphatic side chains (Gly, Ala Val, Leu, Ile)
    iv) cyclic side chains (Phe, Tyr, Trp, His, Pro)
    v) aromatic side chains (Phe, Tyr, Trp)
    vi) acidic side chains (Asp, Glu)
    vii) basic side chains (Lys, Arg, His)
    viii) amide side chains (Asn, Gln)
    ix) hydroxy side chains (Ser, Thr)
    x) sulphur-containing side chains (Cys, Met), and
    xi) amino acids being monoamino-dicarboxylic acids or monoamino-mono-carboxylic-monoamidocarboxylic acids (Asp, Glu, Asn, Gln).

A functional homologue within the scope of the present invention is a polypeptide that exhibits some sequence identity with human Ficolin-3 as identified by SEQ ID NO. 1 or SEQ ID NO: 2, sharing at least 50%, preferably at least 60%, more preferably at least 75%, even more preferably at least 80%, yet more preferably at least 85%, even more preferably at least 90%, yet even more preferably at least 95%, and most preferably at least 99% identity with SEQ ID NO: 1 or SEQ ID NO: 2.

Sequence identity can be calculated using a number of well-known algorithms and applying a number of different gap penalties. The sequence identity may be calculated relative to full-length SEQ ID NO. 1 or SEQ ID NO: 2. In the alternative, it may be calculated relative to SEQ ID NO. 1, or SEQ ID NO: 2 wherein the sequence encoding the signal peptide is not included. Without being bound by theory, the signal peptide is predicted to comprise amino acids 1 to 20 of SEQ ID NO. 1 or SEQ ID NO: 2. Any sequence alignment tool, such as but not limited to FASTA, BLAST, or LALIGN may be used for searching homologues and calculating sequence identity. Moreover, when appropriate any commonly known substitution matrix, such as but not limited to PAM, BLOSSUM or PSSM matrices, may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Complement Activation

The complement system is a biochemical cascade that helps clear pathogens from an organism. It is part of the larger immune system that is not adaptable and does not change over the course of an individual's lifetime; as such it belongs to the innate immune system.

As described herein above three biochemical pathways activate the complement system: the classical complement pathway, the alternative complement pathway, and the lectin pathway. These three pathways converge at the component C3. The terminal complement pathway consists of all proteins activated after C3, and results into assembly of the C5-9 group of proteins into the membrane attack complex (MAC). The MAC exerts powerful killing activity by creating perforations in cellular membranes.

Defects in the complement system may lead to a partial or complete blockade of the complement activation cascade. Depending on the level of the defect, either the induction phase or the effector phase of complement activation may be hampered, and the defect may affect more than one pathway. An impaired function of the complement system may occur due to genetic defects, or due to acquired deficiencies of complement components. Acquired complement deficiencies may occur due to formation of auto antibodies to complement components or due to excessive complement consumption. Genetic complement deficiencies have been described at all levels of the system.

Most complement defects are associated with disease, ranging from a relatively mild increase in the susceptibility to infections to the occurrence of a severe systemic autoimmune syndrome. Furthermore, an impaired complement function is associated with the occurrence of flares in patients with systemic lupus erythematosus (SLE).

Therefore, functional assays to measure complement activity in human serum have a clear diagnostic and prognostic value.

In a preferred embodiment of the invention complement is activated via the lectin pathway, in a more preferred embodiment the lectin pathway is activated by a ficolin and in a most preferred embodiment the lectin pathway is activated by ficolin-3.

Complement activation may be detected by the deposition of one or more of C2, C3, C4 and/or a C5 cleavage product and/or by detecting any of the terminal complement complexes C6, C7, C8 or C9.

In specific embodiments of the present invention complement activation and/or deposition is detected in a sample by the detection of a C2, C3, C4 and/or a C5 cleavage product and/or by detecting any of the terminal complement complex components C5b, C6, C7, C8 or C9 and/or by direct detection of terminal complement complex C5b-9 by for example an antibody against a neoepitope in the complex, which is not present on any of the individual proteins.

Briefly, the lectin pathway is activated by binding mannose-binding lectin (MBL) or Ficolins to different sugar or acetylated residues on the pathogen surface, which activates the MBL-associated serine proteases, MASP-1, and MASP-2, which then split C4 into C4a and C4b and C2 into C2a and C2b. C4b and C2a then bind together to form the C3-convertase (C4b2a complex), which promotes cleavage of C3 into C3a and C3b; C3b later joins with C4b2a (the C3 convertase) to make C5 convertase (C4bC2aC3b complex). C3c and C4c are not part of the convertases. C3b may be cleaved into C3b and C3d. C5 may be cleaved into C5a and C5b where C5b forms a part of the terminal C5b-C9 complex. C3 and C4 are cleaved into C4a and C4b and C3a and C3b respectively. C4 and C3 carry an internal thiolester which may break during activation and form covalent bridges with acceptor sites. C5 on the other hand will become hydrophobis during activation and even more so upon formation of the C5b-C9 complex which can then bind to a surface such as a plastic surface.

In specific embodiments complement activation and/or deposition may be detected by a cleavage assay selected from the group consisting of C2 cleavage assay and/or a C3 cleavage assay and/or a C4 cleavage assay and a C5 cleavage assay.

Petersen et al., (2001) for example describes a C4 cleavage assay and is hereby incorporated by reference.

Garred et al., (1988) describes an assay for the detection of a C3 neoepitope, which may also be used as an indicator of complement activation within the present invention and is hereby incorporated by reference Mollnes, T E., et al., (1984) describes an assay for the detection and quantification of the C5b-C9 complex which may also be used as an indicator of complement activation within the present invention and is hereby incorporated by reference.

Complement activation and/or deposition may be detected by the detection of a cleavage product selected from the group consisting of C2, C3, C4 and C5 cleavage products.

Specifically the C2, C3, C4 and/or C5 cleavage product and/or the terminal complement complexes C5b, C6, C7, C8 or C9 may be detected using a ligand specific for the cleavage product or the terminal complement complex, labelled directly or indirectly with a detectable marker.

In some embodiments of the present invention the ligand specific for the cleavage product or the terminal complement complex is an antibody or a binding fragment of an antibody.

Any C2, C3, C4 and/or C5 cleavage product may be detected as an indicator of complement activation and/or deposition.

In a preferred embodiment complement activation may be detected by detection of the C4 cleavage product C4c. The ligand may thus be an anti-C4c antibody or a binding fragment of an anti-C4c antibody.

In other embodiments other C2, C3, C4 and/or C5 cleavage products may be detected as an indicator of complement activation and/or deposition.

In one such embodiment complement activation may detected by detection of the C4 cleavage product C4a. The ligand may thus be an anti-C4a antibody or a binding fragment of an anti-C4a antibody.

In another embodiment complement activation may be detected by detection of the C4 cleavage product C4b. The ligand may thus be an anti-C4b antibody or a binding fragment of an anti-C4b antibody.

In another embodiment complement activation may be detected by detection of the C3 cleavage product C3a. The ligand may thus be an anti-C3a antibody or a binding fragment of an anti-C3a antibody.

In another embodiment complement activation may be detected by detection of the C3 cleavage product C3b. The ligand may thus be an anti-C3b antibody or a binding fragment of an anti-C3b antibody.

In another embodiment complement activation may be detected by detection of the C3 cleavage product C3c. The ligand may thus be an anti-C3c antibody or a binding fragment of an anti-C3c antibody.

In another embodiment complement activation may be detected by detection of the C3 cleavage product C3d. The ligand may thus be an anti-C3d antibody or a binding fragment of an anti-C3d antibody.

In another embodiment complement activation may be detected by detection of the C5 cleavage product C5a. The ligand may thus be an anti-C5a antibody or a binding fragment of an anti-C5a antibody.

In another embodiment complement activation may be detected by detection of the C5 cleavage product C5b. The ligand may thus be an anti-C5b antibody or a binding fragment of an anti-C5b antibody.

Activation and/or deposition of complement may also be detected by detection of any of the terminal complement complexes C5b, C6, C7, C8 or C9.

In one such embodiment complement activation may detected by detection of C6. The ligand may thus be an anti-C6 antibody or a binding fragment of an anti-C6 antibody.

In another embodiment complement activation may be detected by detection of C7. The ligand may thus be an anti-C7 antibody or a binding fragment of an anti-C7 antibody.

In another embodiment complement activation may be detected by detection of C8. The ligand may thus be an anti-C8 antibody or a binding fragment of an anti-C8 antibody.

In another embodiment complement activation may be detected by detection of C9. The ligand may thus be an anti-C9 antibody or a binding fragment of an anti-C9 antibody.

Antibodies

The methods described herein uses ligands specific for the cleavage product or the terminal complement complex as described herein above, labelled directly or indirectly with a detectable marker In preferred embodiments of the invention the ligand may be an antibody or a binding fragment of an antibody.

The antibody may be any type of antibody known in the art, for example a polyclonal or a monoclonal antibody derived from a mammal or a synthetic antibody, such as a single chain antibody or hybrids comprising antibody fragments. In addition functional equivalents of antibodies may be antibody fragments, in particular epitope binding fragments. Furthermore, antibodies or functional equivalent thereof may be small molecule mimicking an antibody. Naturally occurring antibodies are immunoglobulin molecules consisting of heavy and light chains.

Monoclonal antibodies (Mab's) are antibodies, wherein every antibody molecule are similar and thus recognises the same epitope. Monoclonal antibodies are in general produced by a hybridoma cell line. Methods of making monoclonal antibodies and antibody-synthesizing hybridoma cells are well known to those skilled in the art. Antibody producing hybridomas may for example be prepared by fusion of an antibody producing B lymphocyte with an immortalized B-lymphocyte cell line. Monoclonal antibodies according to the present invention may for example be prepared as described in Antibodies: A Laboratory Manual, By Ed Harlow and David Lane, Cold Spring Harbor Laboratory Press, 1988. Said monoclonal antibodies may be derived from any suitable mammalian species, however frequently the monoclonal antibodies will be rodent antibodies for example murine or rat monoclonal antibodies.

Polyclonal antibodies is a mixture of antibody molecules recognising a specific given antigen, hence polyclonal antibodies may recognise different epitopes within said antigen. In general polyclonal antibodies are purified from serum of a mammal, which previously has been immunized with the antigen. Polyclonal antibodies may for example be prepared by any of the methods described in Antibodies: A Laboratory Manual, By Ed Harlow and David Lane, Cold Spring Harbor Laboratory Press, 1988. Polyclonal antibodies may be derived from any suitable mammalian species, for example from mice, rats, rabbits, donkeys, goats, sheep. The antibody is preferably not derived from a non-mammalian species, i.e. the antibody is for example preferably not a chicken antibody.

In one embodiment of the invention the antibody is a human antibody, such as a human monoclonal antibody. Alternatively, the antibody may be a humanised antibody. Humanised antibodies are in general chimeric antibodies comprising regions derived from a human antibody and regions derived from a non-human antibody, such as a rodent antibody. Humanisation (also called Reshaping or CDR-grafting) is a well-established technique for reducing the immunogenicity of monoclonal antibodies (mAbs) from xenogeneic sources (commonly rodent) and for improving their activation of the human immune system, frameworks in which to graft the rodent CDRs. The term "humanised antibody molecule" (HAM) is used herein to describe a molecule having an antigen binding site derived from an immunoglobulin from a non-human species, whereas some or all of the remaining immunoglobulin-derived parts of the molecule is derived from a human immunoglobulin. The antigen binding site may comprise: either a complete variable domain from the non-human immunoglobulin fused onto one or more human constant domains; or one or more of the complementarity determining regions (CDRs) grafted onto appropriate human framework regions in the variable domain. One method for humanising MAbs related to production of chimeric antibodies in which an antigen binding site comprising the complete variable domains of one antibody are fused to constant domains derived from a second antibody, preferably a human antibody.

Functional equivalents of antibodies may be a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Fab is the fragment that contains a monovalent antigen-binding fragment of an antibody molecule. A Fab fragment can be produced by digestion of whole antibody with the enzyme papain to yield an intact light chain and a portion of one heavy chain.

Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(Fab')$_2$ is the fragment of an antibody that can be obtained by treating whole antibody with the enzyme pepsin without subsequent reduction. F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The antibody can also be a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding.

A monovalent antibody means that an antibody molecule is capable of binding a single molecule of the antigen, and thus is not able of antigen crosslinking. For a monovalent antibody, the immunoglobulin constant domain amino acid residue sequences comprise the structural portions of an antibody molecule known in the art as CH1, CH2, CH3 and CH4. Furthermore, insofar as the constant domain can be either a heavy or light chain constant domain ($C_H$ or $C_L$, respectively. Light chain constant domains are capable of disulfide bridging to either another light chain constant domain, or to a heavy chain constant domain. In contrast, a heavy chain constant domain can form two independent disulfide bridges, allowing for the possibility of bridging to both another heavy chain and to a light chain, or to form polymers of heavy chains.

Multivalent antibodies have at least two binding domains. The binding domains may have specificity for the same ligand or for different ligands.

A bispecific molecule can be a single chain bispecific molecule, such as a single chain bispecific antibody, a single chain bispecific molecule comprising one single chain antibody and a binding domain, or a single chain bispecific molecule comprising two binding domains. Multispecific molecules can also be single chain molecules or may comprise at least two single chain molecules.

In a particular embodiment of the invention the antibody is an antibody specific for Ficolin-3 or a binding fragment of an antibody specific for Ficolin-3.

In another particular embodiment of the invention the antibody is an antibody specific for a downstream component of Ficilon-3 dependent activation of complement, which is selected from the group consisting of MASP-1, MASP-2, MASP-3, C2, C3, C4, C5, C6, C7, C8, C9, complement regulatory protein factor I, Factor H, C1 inhibitor and C4 binding protein.

Ligands/labels

The methods described herein uses ligands specific for the cleavage product or the terminal complement complex as described herein above, labelled directly or indirectly with a detectable marker.

The detectable marker may be any detectable marker including but not limited to enzymatic, fluorescent, luminescent and radioactive markers.

The detectable marker may be selected from the group consisting of horse radish peroxidise (HRP), alkaline phosphatase, biotin, europium, fluorescein isothiocyanate, a fluorescent protein or a radiolabel.

A reagent for detection of Ficolin-3 binding to an acetylated molecule may comprise a ligand capable of being labelled directly or indirectly with a detectable marker, suitably the ligand is an antibody or a binding fragment of an antibody, most suitably an antibody or a binding fragment thereof specific for one or more of C2, C3, C4 and/or a C5 cleavage product and/or by detecting any of the terminal complement complex components C5b, C6, C7, C8 or C9 and/or the C5b-9 complex and/or any the downstream components such as MASP-1, MASP-2, MASP-3, C2, C3, C4, C5, C6, C7, C8, C9, complement regulatory protein factor I, Factor H, C1 inhibitor and C4 binding protein. Detection of activation of complement via Ficolin-3 binding to an acetylated molecule may be performed using ligand labelled directly with a detectable marker, or using ligand labelled indirectly with a detectable marker. A suitable detectable marker would be a fluorescent, luminescent or radioactive marker which can be selected from the group comprising alkaline horse radish peroxidise (HRP), and the horse radish peroxidise (HRP), may be detected using a chromogenic substrate, preferably Ortho-Phenylenediamine (OPD).

In one embodiment wherein the detectable marker is detected via the use of fluorescence microscopy, the detectable marker may be fluorescein isothiocyanate (FITC).

In preferred embodiments of the invention the assay and/or methods of the invention may be performed in multiwell format, preferably 96 well format.

In particular embodiments of the invention the assays and/or methods of the invention may be carried out in a high throughput format.

Any high throughput format may be used including but not limited to ELISA based assays, europium based assays, flow cytometry including plastic/polystyrene beads based assays, radioimmune assays (RIA), nitrocelluose matrices, Polyvinylidene Fluoride (PVDf) and glass.

Horseradish peroxidase enzyme linked to the nonspecific agent could be used in the manner of the ELISA type assay systems. Thereafter, o-phenylenediamine is supplied as a substrate and the appearance of product detected by optical density measurements at approximately 490 nm.

Assay

The methods and assays described herein are based on the novel finding that Ficolin-3 binds to acetylated molecules.

Acetylation of the N-terminal alpha-amine of proteins is a widespread modification in eukaryotes. 80-90% of human proteins are modified in this manner.

Any acetylated molecule may be used in the assays and methods of the present invention, include but are not limited to any protein or any carbohydrate, including any one or more proteins selected from the group consisting of ovalbumin, bovine serum albumin and human serum albumin.

In specific embodiments of the invention the acetylated molecule may be immobilised on a support. The support may be any support, such as for example a solid support.

The support on which the acetylated molecule is immobilised may comprise one or more wells on a multiwell plate. A reagent for detection of one or more of C2, C3, C4 and/or a C5 cleavage product and/or by detecting any of the terminal complement complex components C5b, C6, C7, C8 or C9 and/or the C5b-9 complex and/or any the downstream components such as MASP-1, MASP-2, MASP-3, C2, C3, C4, C5, C6, C7, C8, C9, complement regulatory protein factor I, Factor H, C1 inhibitor and C4 binding protein may comprise a ligand capable of being labelled directly or indirectly with a detectable marker. The ligand can be an antibody or a binding fragment of an antibody. In one form of the kit the ligand specifically binds the C4 cleavage product C4c.

The immobilisation techniques will depend largely upon the nature of the solid support selected but such processes are typically well-known and need not be detailed at length here.

In a specific embodiment the specific binding of Ficolin-3 complex to the acetylated molecule is detected using a ligand labelled directly or indirectly with a detectable marker.

In some embodiments of the invention it may be useful to prevent non-specific activation of the classical pathway and/or the alternative pathway and/or of non-Ficolin-3 dependent activation of the lectin pathway.

In specific embodiments the activation of the classical pathway and/or the alternative pathway and/or any non-Ficolin-3 mediated activation of the lectin pathway may be prevented by contacting the sample with an inhibitor of the classical pathway and/or the alternative pathway and/or any non-Ficolin-3 mediated activation of the lectin pathway.

In a particular embodiment the inhibitor may be an inhibitor of the lectin pathway and may be an antibody selected from the group consisting of anti-MBL, anti-Ficolin-1 and anti-Ficolin-2.

In another specific embodiment the inhibitor may be an inhibitor of the classical pathway, including but not limited to polyanethole sulphonic acid, any anti-C1q antibody, any anti-C1r antibody and any anti-C1s antibody.

In a particular embodiment the activation of the classical pathway and/or the alternative pathway and/or any non-Ficolin-3 mediated activation of the lectin pathway may be prevented by depletion of another activator using GlcNAc-agarose beads or matrix conjugated antibodies against ficolin-1 and ficolin-2.

Specifically, the activation of the classical pathway and/or the alternative pathway and/or any non-Ficolin-3 mediated activation of the lectin pathway may be prevented by depletion of Ficolin-2 using GlcNAc-agarose beads or an antibody against ficolin-2.

Kit of Parts

All the materials and reagents required for detecting Ficolin-3 dependent activation of the lectin pathway of complement and/or for identifying an abnormality in Ficolin-3 and/or for identifying an abnormality in any downstream components of the Ficilon-3 dependent activation of complement according to the present invention can be assembled together in a kit, such kit includes at least elements in aid of assessing Ficolin-3 dependent activation of the lectin pathway of complement and/or for identifying an abnormality in Ficolin-3 and/or for identifying an abnormality in any downstream components of the Ficilon-3 dependent activation of complement in a biological sample obtained from an individual, and the instruction on how to do so.

In a particular embodiment the kit for detecting Ficolin-3 dependent activation of the lectin pathway of complement and/or for identifying an abnormality in Ficolin-3 and/or for identifying an abnormality in any downstream components of the Ficilon-3 dependent activation of complement may comprise:
- a. an acetylated molecule immobilised on a support,
- b. full serum as a positive control
- c. a reagent or reagents for detection of a complement cleavage product and/or by detecting any terminal complement complex, and
- d. one or more buffers which allows binding of ficolin-3 to an acetylated molecule
- e. optionally standard serum or purified Ficolin-3/MASP complex suitable for generation of a standard curve, and,
- f. optionally instructions for use of the kit.

Specifically the kit may comprise a reagent for detection of a C2, C3, C4 and/or a C5 cleavage product or a terminal complement complex component such as C5b, C6, C7, C8, C9 or a reagent detecting the formation of the terminal C5b-C9 complement complex or clusterin or vitronectin, wherein the reagent may comprise a ligand capable of being labelled directly or indirectly with a detectable marker.

In another specific embodiment the kit may comprise a reagent for detection of a terminal complement complex selected from the group consisting of C5b, C6, C7, C8 or C9

In specific embodiments the ligand may be an antibody or a binding fragment of an antibody.

In one embodiment the ligand specifically binds the C4 cleavage product C4b and C4c and C4d.

In another embodiment the ligand specifically binds the C4 cleavage product C4a.

In another embodiment the ligand specifically binds the C4 cleavage product C4b.

In another embodiment the ligand specifically binds the C3 cleavage product C3a.

In another embodiment the ligand specifically binds the C3 cleavage product C3b.

In another embodiment the ligand specifically binds the C3 cleavage product C3c.

In another embodiment the ligand specifically binds the C3 cleavage product C3d.

In another embodiment the ligand specifically binds the C5 cleavage product C5a.

In another embodiment the ligand specifically binds the C5 cleavage product C5b.

In another embodiment the ligand specifically binds the terminal complement complex C6.

In another embodiment the ligand specifically binds the terminal complement complex C7.

In another embodiment the ligand specifically binds the terminal complement complex C8.

In another embodiment the ligand specifically binds the terminal complement complex C9.

In another embodiment the ligand specifically binds the C5b-9 complex.

Yet another embodiment of the invention relates to a kit detecting Ficolin-3 comprising:
- a. an acetylated molecule immobilised on a support, and
- b. a reagent or reagents for detection of Ficolin-3 binding to said acetylated molecule, and
- c. optionally, standard serum or purified Ficolin-3/MASP complex or purified Ficolin-3, suitable for generation of a standard curve, and
- d. optionally, instructions for use of the kit In a particular embodiment the reagent for detection of Ficolin-3 binding to the acetylated molecule comprises a ligand capable of being labelled directly or indirectly with a detectable marker.

In another embodiment the ligand is an antibody or a binding fragment of an antibody.

In another embodiment the antibody is an antibody specific for Ficolin-3 or a binding fragment of an antibody specific for Ficolin-3.

In another embodiment the antibody is SCN 334 or a fragment thereof that specifically binds Ficolin-3.

In another embodiment the ligand is labelled directly with a detectable marker.

In another embodiment the ligand is labelled indirectly with a detectable marker.

In another embodiment the detectable marker is an enzymatic, fluorescent, luminescent or radioactive marker.

In another embodiment the detectable marker is selected from the group comprising horse radish peroxidise (HRP), alkaline phosphatase, biotin, europium, fluorescein isothiocyanate, a fluorescent protein or a radiolabel.

In another embodiment the detectable marker is horse radish peroxidise (HRP), and the horse radish peroxidise (HRP), is detected using a chromogenic substrate, preferably Ortho-Phenylenediamine (OPD).

In another embodiment the support is one or more wells on a multiwell plate.

REFERENCES

Akaiwa, M., Yae, Y., Sugimoto, R., Suzuki, S. O., Iwaki, T., Izuhara, K. and Hamasaki, N. (1999) Hakata antigen, a new member of the Ficolin/opsonin p35 family, is a novel human lectin secreted into bronchus/alveolus and bile. J. Histochem. Cytochem., 47, 777-785.

Endo, Y., Sato, Y., Matsushita, M. and Fujita, T. (1996) Cloning and characterization of the human lectin P35 gene and its related gene. Genomics, 36, 515-521.

Garred; P., Mollnes, T. E., and Lea, T. Quantification in enzyme-linked immunosorbent assay of a C3 neoepitope expressed on activated human complement factor C3. Scand. J. Immunol. 27:329-335, (1988)

Harumiya, S., Takeda, K., Sugiura, T., Fukumoto, Y., Tachikawa, H., Miyazono, K., Fujimoto, D. and Ichijo, H. (1996) Characterization of ficolins as novel elastin-binding proteins and molecular cloning of human ficolin-1. J. Biochem. (Tokyo), 120, 745-751.

Honore, C., Rorvig, S., Munthe-Fog, L., Hummelshoj, T., Madsen, H. O., Borregaard, N., and Garred. P. The innate pattern recognition molecule Ficolin-1 is secreted by monocytes/macrophages and is circulating in human plasma Mol. Immunol. 45 (10):2782-2789, 2008

Hummelshoj, T., Munthe-Fog, L., Madsen, H. O., Fujita, T., Matsushita, M., and Garred, P. Polymorphisms in the FCN2 gene determine serum variation and function of Ficolin-2. Hum. Mol. Genet. 14 (12):1651-1658, 2005

Kilpatrick, D. C., Fujita, T. and Matsushita, M. (1999) P35, an opsonic lectin of the ficolin family, in human blood from neonates, normal adults, and recurrent miscarriage patients. Immunol. Lett., 67, 109-112.

Krarup, A., Thiel, S., Hansen, A., Fujita, T. and Jensenius, J. C. (2004) L-ficolin is a pattern recognition molecule specific for acetyl groups. J. Biol. Chem., 279, 47513-47519.

Lu, J., Tay, P. N., Kon, O. L. and Reid, K. B. (1996) Human ficolin: cDNA cloning, demonstration of peripheral blood leucocytes as the major site of synthesis and assignment of the gene to chromosome 9. Biochem. J., 313, 473-478.

Lynch, N. J., Roscher, S., Hartung, T., Morath, S., Matsushita, M., Maennel, D. N., Kuraya, M., Fujita, T. and Schwaeble, W. J. (2004) L-ficolin specifically binds to lipoteichoic acid, a cell wall constituent of gram-positive bacteria, and activates the lectin pathway of complement. J. Immunol., 172, 1198-1202.

Matsushita, M., Endo, Y., Taira, S., Sato, Y., Fujita, T., Ichikawa, N., Nakta, M. and Mizuouchi, T. (1996) A novel human serum lectin with collagen- and fibirinogen-like domains that functions as an opsonin. J. Biol. Chem., 271, 2448-2454.

Matsushita, M., Endo, Y. and Fujita, T. (2000) Cutting edge: complement-activating complex of ficolin and mannose-binding lectin-associated serine protease. J. Immunol., 164, 2281-2284.

Matsushita, M., Fujita, T. (2001) Ficolins and the lectin complement pathway. Immunol. Rev., 180, 78-85

Matsushita, M., Kuraya, M., Hamasaki, N., Tsujimura, M., Shiraki, H. and Fujita, T. (2002) Activation of the lectin complement pathway by H-ficolin (Hakata antigen). J. Immunol., 168, 3502-3506.

Mollnes, T E., et al., Lea, T., and Harboe, M. Detection and quantification of the terminal C5b-9 complex of human complement by a sensitive enzyme-linked immunosorbent assay. Scand. J. Immunol. 20:157-166, (1984)

Petersen S. V., S. Thiel, L. Jensen, R. Steffensen, and J. C. Jensenius (2001) An assay for the mannan-binding lectin pathway of complement activation. J. Immunol. Methods. 257:107.

Munthe-Fog, L., Hummelshoj, T., Ma, Y. J., Hansen, B. E., Koch, C., Madsen, H. O., Skjodt, K., and Garred. P. Characterization of a polymorphism in the coding sequence of FCN3 resulting in a Ficolin-3 (Hakata antigen) deficiency state. *Mol. Immunol.* 45:2660-2666, 2008

Sugimoto, R., Yae, Y., Akaiwa, M., Kitajima, S., Shibata, Y., Sato, H., Hirata, J., Okochi, K., Izuhara, K. and Hamasaki, N. (1998) Cloning and characterization of the Hakata antigen, a member of the Ficolin/opsonin p35 lectin family. J. Biol. Chem., 273, 20721-20727.

Teh, C., Le, Y., Lee, S. H. and Lu, J. (2000) M-ficolin is expressed on monocytes and is a lectin binding to N-acetyl-D-glucosamine and mediates monocyte adhesion and phagocytosis of *Escherichia coli*. Immunology, 101, 225-232

Tsujimura, M., Miyazaki, T., Kojima, E., Sagara, Y., Shiraki, H., Okochi, K. and Maeda, Y. (2002) Serum concentration of Hakata antigen, a member of the ficolins, is linked with inhibition of Aerococcus viridans growth. Clin. Chim. Acta, 325, 139-146.

Yae, Y., Inaba, S., Sato, H., Okochi, K., Tokunaga, F., and Iwanaga, S. (1991) Isolation and characterization of a thermolabile beta-2 macroglycoprotein ('thermolabile substance' or 'Hakata antigen') detected by precipitating (auto) antibody in sera of patients with systemic lupus erythematosus. Biochim. Biophys. Acta, 1078, 369-376.

DETAILED DESCRIPTION OF THE DRAWINGS

Figure 1:
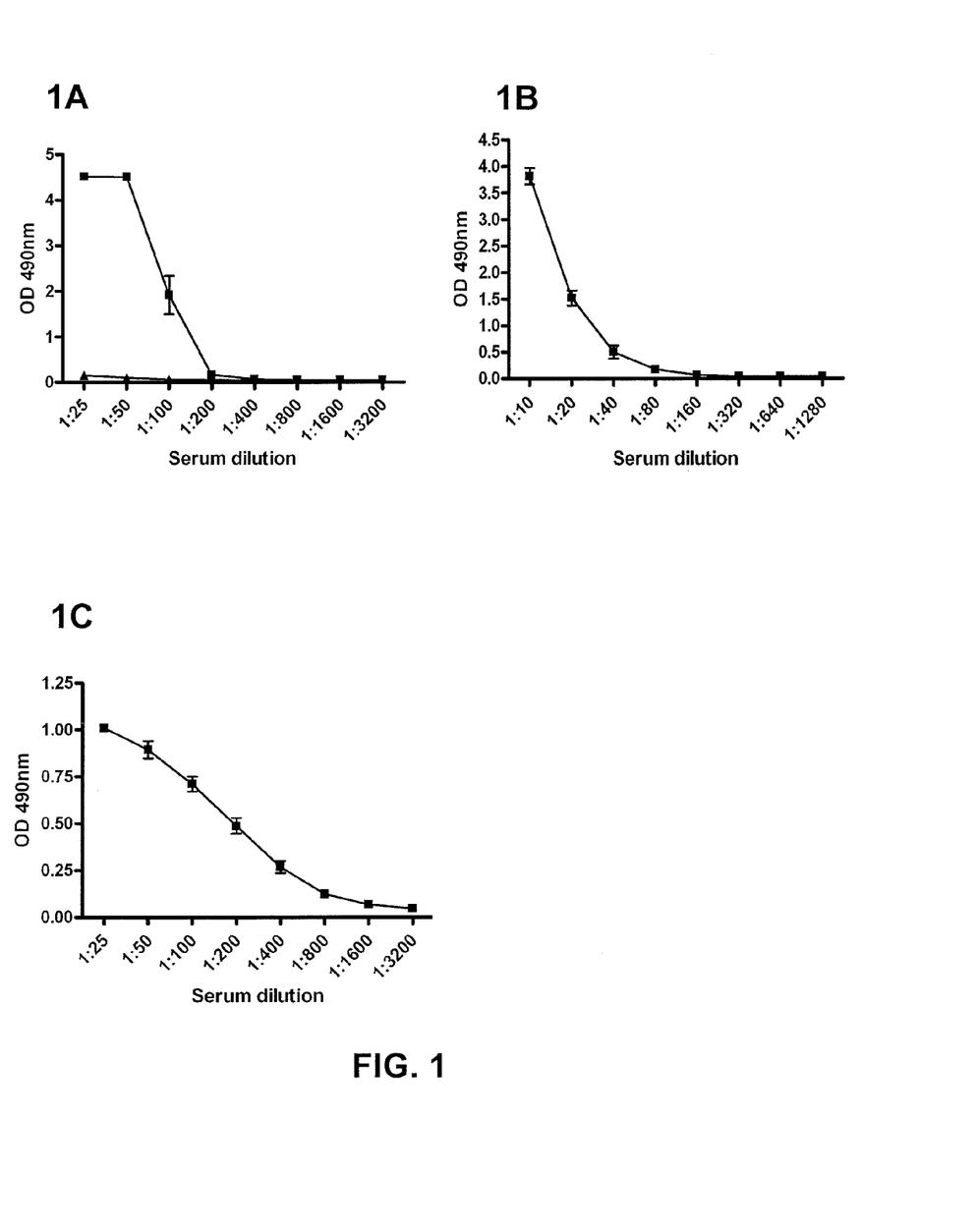
FIG. 1: Complement activation on acetylated BSA.

FIG. 1. (A) Complement activation on acetylated BSA. Acetylated BSA (-■-) or non-acetylated BSA (-▲-) was immobilized onto microtiter plates and subsequently incubated with human serum for 30 min at 37° C. and C4c deposition was assessed. Graph shows the mean±SEM of two individual experiments. (B-C) Ficolin-2 and Ficolin-3 binding to acetylated BSA. Serum was incubated with immobilized acetylated BSA for 3 hours and serum Ficolin-2 (B) and Ficolin-3 (C) bound to acetylated BSA was measured. Graph shows the mean±SEM of two individual experiments.

Figure 2:
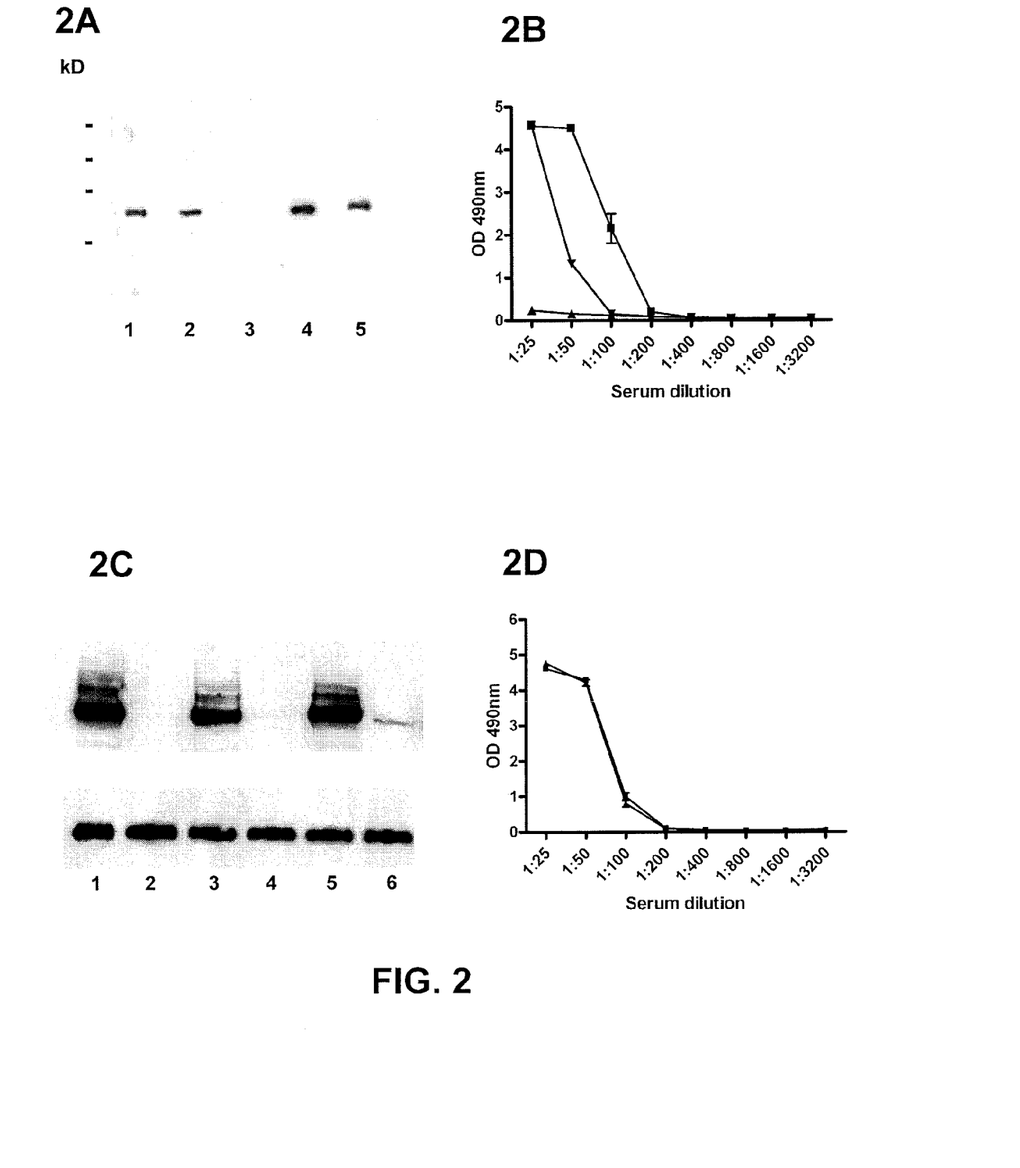
FIG. 2 (A) Western blot of serum Ficolin-3 from FCN3+1637delC homozygous individual and relatives, (B) C4c deposition on acetylated BSA is mediated by Ficolin-3, (C) Depletion of Ficolin-2 from serum using GlcNAc-beads, C4c deposition on acetylated BSA using Ficolin-2 depleted serum.

FIG. 2. (A) Western blot of serum Ficolin-3 from FCN3+1637delC homozygous individual and relatives. Serum proteins were separated by SDS-PAGE under reducing conditions and proteins were blotted onto a nitrocellulose membrane and probed for Ficolin-3. Lane 1. Serum from heterozygous FCN3+1637delC individual. Lane 2. Serum from heterozygous FCN3+1637delC individual. Lane 3 Serum from homozygous FCN3+1637delC individual. Lane 4. Serum from wildtype individual. Lane 5.1 µg/ml recombinant Ficolin-3. Figure representative of two individual experiments. (B) C4c deposition on acetylated BSA is mediated by Ficolin-3. Acetylated BSA coated onto microtiter plates was incubated with human serum for 30 min at 37° C. C4c deposition on acetylated BSA using a human serum pool (-■-), serum from the Ficolin-3 deficient individual (-▲-) or serum from the Ficolin-3 deficient individual reconstituted with 20 µg/ml recombinant Ficolin-3 (-▼-). Graph shows the mean±SEM of three individual experiments. (C) Depletion of Ficolin-2 from serum using GlcNAc-beads. Serum proteins were separated by SDS-PAGE under non-reducing or reducing conditions and proteins were blotted onto a nitrocellulose membrane and probed for Ficolin-2 (upper blot) or Ficolin-3 (lower blot). Depletion of Ficolin-2 was carried out on serum from three individuals. Lane 1, 3 and 5. Serum from three individuals, untreated. Lane 2, 4 and 6. Serum from three individuals, GlcNAc-depleted. (D). C4c deposition on acetylated BSA using Ficolin-2 depleted serum. Ficolin-2 depleted (-■-) or untreated serum (-▼-) was incubated with immobilized acetylated BSA for 30 min at 37° C. C4c deposition was subsequently assessed. Graph shows representative result of three individual experiments using serum from different donors.

Figure 3:
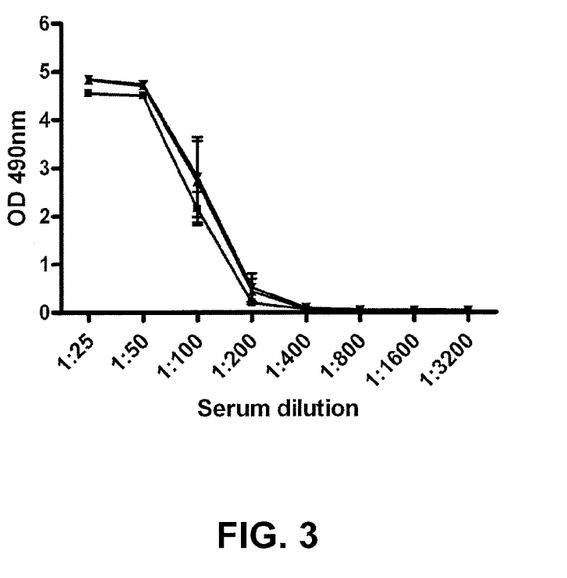
FIG. 3: C4c deposition on immobilized acetylated BSA.

FIG. 3. (A) C4c deposition on immobilized acetylated BSA using a human serum Pool (-■-), serum from a FICOLIN-3 defect individual (-▲-) or serum from a C1q deficient individual (-▼-). Figure shows the mean±SEM of three individual experiments.

EXAMPLES

10% bovine serum albumin (BSA) was diluted 1:1 in a 5.4M sodium acetate solution and incubated on ice for 1 hour. During the incubation, acetic anhydride (Sigma-Aldrich, Broendby, Denmark) was added to the solution at 12 min intervals to a final conc. of 0.5 mM. Following incubation, the sample was desalted with PBS-buffer using amicon ultra-15 centrifugal filter devices (Millipore, Copenhagen, Denmark).

Serum was collected with consent from healthy individuals. Serum was depleted for Ficolin-2 using GlcNAc-agarose beads. Depletion was confirmed using both SDS-PAGE/Western blot and a sandwich ELISA specific for Ficolin-2.

10 µg/ml acetylated BSA or non-acetylated BSA as a control was coated in 96-well maxisorp microtiter plates (Nunc, Roskilde, Denmark) overnight at 4° C. in PBS-buffer. Wells were washed thrice in hepes-buffer (25 mM Hepes, 155 mM NaCl, 5 mM $CaCl_2$, pH=7.4) containing 0.05% tween (hepes-T) and blocked for 1 hour with 200 µl/well hepes-T. Following blocking, the wells were incubated with sera diluted in hepes-T for 30 min at 37° C. and subsequently washed in hepes-T. C4 deposition was detected using a rabbit polyclonal anti-human C4 antibody (DAKO, Glostrup, Denmark) and an HRP-conjugated anti-rabbit IgG (GE healthcare, Buckinghamshire, United Kingdom). The plates were developed with OPD substrate (DAKO, Glostrup, Denmark) and $H_2O_2$ for 15 min and the enzymatic reaction was terminated by adding 1M $H_2SO_4$ to the wells. The optical density of the wells was measured at 490 nm.

Results

Incubating serum in different dilutions on immobilized acetylated BSA mediated C4c deposition onto the plate (FIG. 1A). Very little C4c deposition was observed on non-acetylated BSA at the two highest serum concentrations (FIG. 1A). These results suggest that immobilized acetylated BSA serves as a complement-activating ligand. Ficolins have been known to bind acetylated compounds and was assumed to be the molecules involved in the activation of complement on acetylated BSA. To assess this, we measured binding of serum Ficolin-2 and Ficolin-3 to acetylated BSA. As seen in FIGS. 1B and 10, both Ficolin-2 and Ficolin-3 from serum bound to acetylated BSA. However, it should be noted that in the experimental setup, serum was incubated for three hours with immobilized acetylated BSA. In comparison, when measuring the C4c deposition, serum is only incubated with immobilized acetylated BSA for thirty minutes. When measuring binding of Ficolins from serum incubated with immobilized acetylated BSA for only thirty minutes, almost no Ficolin-2 binding was observed, while a considerable reduction was seen in the Ficolin-3 binding (data not shown).

To assess which of the Ficolins was involved in the activation of complement on immobilized acetylated BSA, we utilized serum from an individual homozygote for a frameshift mutation in the FCN3 gene, resulting in Ficolin-3 deficiency (FIG. 2A). Serum from the Ficolin-3 deficient individual and as a control a serum pool was applied to the immobilized acetylated BSA and C4c deposition was assessed. As expected, the serum pool mediated deposition of C4c onto the microtiter plate, demonstrating complement activation. However, C4c deposition was lacking when the serum from the Ficolin-3 deficient individual was used (FIG. 2B). Only very little deposition was seen at the highest serum concentration used comparable to background levels (FIG. 2B). The Ficolin-3 deficient individual showed normal complement activation mediated by the classical and alternative pathway. Furthermore, the FICOLIN-3-specific complement activation on mannan was also functional and the Ficolin-2 concentration was within normal range, demonstrating that no other complement deficiencies were present in the Ficolin-3 deficient individual (data not shown). In accordance with this, reconstituting serum from the Ficolin-3 deficient individual with recombinant Ficolin-3 lead to the recovery of the C4c deposition onto immobilized acetylated BSA (FIG. 2B). Thus, using serum from a Ficolin-3 deficient individual lead us to believe that under the experimental settings used, Ficolin-3 is primary molecule mediating complement activation on acetylated BSA.

To further validate that Ficolin-3 is the molecule responsible for activating complement on immobilized acetylated BSA, we depleted Ficolin-2 from serum using GlcNAc-beads (GlcNAc is a known ligand for Ficolin-2 but not Ficolin-3). Depletion of Ficolin-2 from serum obtained from three individuals was almost complete, while no influence was seen on the serum levels of Ficolin-3 (FIG. 2C). This was also confirmed using sandwich ELISA specific for Ficolin-2 and Ficolin-3 (data not shown). The Ficolin-2 depleted and untreated serum was incubated with immobilized acetylated BSA and C4c deposition was assessed. As shown in FIG. 2D, depletion of Ficolin-2 from serum had no influence on the deposition of C4c on immobilized BSA. Depleting Ficolin-2 from serum using a Ficolin-2 specific antibody has further validated these results (data not shown). In addition, depleting Ficolin-3 from serum using a specific antibody results in a significantly reduction of C4c deposition on immobilized acetylated BSA (data not shown), again confirming that Ficolin-3 is the primary molecule mediating C4c deposition on immobilized BSA.

As mentioned, the Ficolin-3 deficient individual had functional classical pathway and MBL-mediated activation. Thus, it appears that C1q and MBL has no activity towards immobilized acetylated BSA. To test this, we applied serum from a C1q deficient individual and serum from a MBL defect individual to immobilized acetylated BSA and measured C4c deposition. As seen in FIG. 3A, no significant difference was seen in the C4c deposition from the C1q deficient and MBL defect serum compared to a human serum pool.

The invention claimed is:

1. A method for detecting Ficolin-3 binding to a Ficolin-3 ligand, the method comprising:
   detecting a complex of Ficolin-3 and a Ficolin-3 ligand, wherein the Ficolin-3 ligand is an acetylated protein that is immobilized on a support.

2. The method according to claim 1, wherein detecting a complex of Ficolin-3 and a Ficolin-3 ligand comprises:
   contacting the Ficolin-3 ligand with a sample of blood, serum, plasma, another body fluid, or an extract thereof, under conditions that permit specific binding of Ficolin-3 to Ficolin-3 ligand;
   and,
   quantifying the complex of the Ficolin-3 and the Ficolin-3 ligand.

3. The method according to claim 2, further comprising determining in the sample complement activation and/or deposition by the detection of a C2, C3, C4 and/or a C5 cleavage product and/or by detection of any of the terminal complement components C5b, C6, C7, C8 or C9 and/or the C5b-9 complex.

4. The method according to claim 3 wherein the cleavage product or the terminal complement component or complex is detected with an antibody or a binding fragment of an antibody specific for the cleavage product or the terminal complement component or complex.

5. The method according to claim 2, further comprising preventing activation of the classical complement pathway and/or the alternative complement pathway and/or any non-Ficolin-3 mediated activation of the lectin pathway of complement in the sample.

6. The method according to claim 1, wherein the Ficolin-3 ligand is selected from the group consisting of ovalbumin, bovine serum albumin, and human serum albumin.

7. The method according to claim 1, wherein further comprising:
   detecting an abnormality in any downstream component of the Ficolin-3 depending activation of complement, wherein the downstream component of Ficolin-3 dependent activation of complement is selected from the group consisting of MASP-1, MASP-2, MASP-3, C2, C3, C4, C5, C6, C7, C8, C9, complement regulatory protein factor I, Factor H, C1 inhibitor, and C4 binding protein.

8. The method according to claim 1, wherein detecting a complex of Ficolin-3 and a Ficolin-3 ligand is performed in multiwell format.

9. A kit suitable for performing the method according to claim 1, the kit comprising:
   an acetylated proteinaceous Ficolin-3 ligand immobilized on a support,
   a positive control,
   a reagent or reagents for detection of a complement cleavage product and/or for detecting any terminal complement complex component or downstream component, and
   one or more buffers which allows binding of Ficolin-3 to the acetylated Ficolin-3 ligand.

10. The kit of claim 9, wherein the terminal complement complex component is selected from the group consisting of C5b, C6, C7, C8 or C9, the terminal C5b-C9 complement complex or the membrane attack complex MAC.

11. The kit of claim 9, comprising an antibody or a binding fragment of an antibody directed against a terminal complement complex component selected from the group consisting of C5b, C6, C7, C8 or C9, the terminal C5b-C9 complement complex or the membrane attack complex MAC.

12. The kit of claim 9, comprising an antibody or a binding fragment of an antibody directed against Ficolin-3.

13. The kit of claim 9, wherein the support is selected from the group consisting of a multiwell plate, a 96 well ELISA plate, and plastic or polystyrene beads.

14. The method according to claim 1, wherein the method comprises an ELISA based assay, a europium based assay, a radioimmune assay, a flow cytometry assay, plastic bead assay, or a polystyrene bead assay.

* * * * *